(12) United States Patent
Danielmeier et al.

(10) Patent No.: US 6,911,501 B1
(45) Date of Patent: Jun. 28, 2005

(54) PROCESS FOR PREPARING ASPARTATES

(75) Inventors: Karsten Danielmeier, Sollingen-Burg (DE); Charles A. Gambino, McDonald, PA (US); Rolf Gertzmann, Leverkusen (DE); Richard R. Roesler, Wexford, PA (US); Terrell D. Wayt, Moundsville, WV (US); Michele E. Vargo, Pittsburgh, PA (US); Edward P. Squiller, Bridgeville, PA (US); Karen M. Henderson, Coraopolis, PA (US)

(73) Assignees: Bayer MaterialScience LLC, Pittsburgh, PA (US); Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 10/761,643

(22) Filed: Jan. 21, 2004

(51) Int. Cl.$^7$ .................. C08F 283/04; C08G 73/10
(52) U.S. Cl. .................. 525/422; 528/310; 528/335; 528/338; 528/339; 528/340; 528/422; 525/420; 525/421; 525/424; 525/540
(58) Field of Search ................ 528/310, 335, 528/338, 339, 340, 422; 525/420, 421, 422, 424, 540

(56) References Cited

U.S. PATENT DOCUMENTS

| | | |
|---|---|---|
| 5,126,170 A | 6/1992 | Zwiener et al. .......... 427/385.5 |
| 5,214,086 A | 5/1993 | Mormile ................... 524/237 |
| 5,236,741 A | 8/1993 | Zwiener et al. .......... 427/385.5 |
| 5,243,012 A | 9/1993 | Wicks et al. ................ 528/58 |
| 5,364,955 A | 11/1994 | Zwiener et al. ............. 556/418 |
| 5,412,056 A | 5/1995 | Zwiener et al. ............... 528/73 |
| 5,489,704 A | 2/1996 | Squiller et al. .............. 560/35 |
| 5,559,204 A | 9/1996 | Squiller et al. .............. 528/84 |
| 5,623,045 A | 4/1997 | Zwiener et al. .............. 528/68 |
| 5,736,604 A | 4/1998 | Luthra ...................... 524/591 |
| 5,821,326 A | 10/1998 | Kurek et al. ................ 528/332 |
| 5,847,195 A | 12/1998 | Roesler ..................... 550/35 |
| 6,005,062 A | 12/1999 | Hansen et al. ................ 528/68 |
| 6,183,870 B1 | 2/2001 | Hergenrother et al. ... 428/423.1 |

FOREIGN PATENT DOCUMENTS

EP  667 362  8/1995

OTHER PUBLICATIONS

Houben Weyl, Meth. D. Org. Chemie, vol. 11/1, month unavailable 1957, pp. 272–277, F. Müller: "Amine durch Anlagerungsreaktionen".

Usp. Chimii, month unavailable 1969, pp. 1933–1963, C.H. Cymuhob et al.

*Primary Examiner*—Samuel A. Acquah
(74) *Attorney, Agent, or Firm*—Joseph C. Gil

(57) ABSTRACT

The present invention relates to novel aspartates, their method of production and the use of these aspartates as reactive components for polyisocyanates in two-component polyurethane coating compositions and for preparing polyurethane prepolymers. The aspartates are prepared by first reacting a di- or polyamine with an unsaturated ester and then reacting the resultant product with a maleimide.

11 Claims, No Drawings

PROCESS FOR PREPARING ASPARTATES

BACKGROUND OF THE INVENTION

The present invention relates to novel aspartates, a process for preparing them from primary amines and maleates and to their use as reactive components for polyisocyanates in two-component polyurethane coating compositions and for preparing polyurethane prepolymers.

Two-component coating compositions which contain, as binder, a polyisocyanate component combined with one or more isocyanate-reactive components are known. They are suitable for preparing high quality coatings which are hard, elastic, abrasion resistant, solvent resistant and weather resistant.

Secondary polyamines which contain ester groups have become established in the two-component surface coating industry. They are particularly suitable, in combination with lacquer polyisocyanates, as binders in low-solvent or solvent-free, high solids coating compositions because they provide rapid curing of the coatings at low temperatures.

These secondary polamines are polyaspartates and are described, e.g., in U.S. Pat. Nos. 5,126,170, 5,214,086, 5,236,741, 5,243,012, 5,364,955, 5,412,056, 5,623,045, 5,736,604, 6,183,870, 6,355,829, 6,458,293 and 6,482,333 and published European Patent Application 667,362. In addition, aspartates containing aldimine groups are also known (see U.S. Pat. Nos. 5,489,704, 5,559,204 and 5,847,195). Secondary aspartic acid amide esters are also known (see U.S. Pat. No. 6,005,062). Their use as the only isocyanate-reactive component or mixed with other isocyanate-reactive components in two-component coating compositions are also described in the above-identified patents.

The process for preparing these polyaspartates is the reaction of the corresponding primary polyamines with maleates or fumarates corresponding to the formula

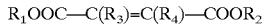

wherein $R_1$, $R_2$, $R_3$ and $R_4$ are identical or different organic groups, resulting in the formation of secondary polyamines. Due to stearic, structural and electronic effects, these secondary amino groups have sufficiently reduced reactivity towards isocyanate groups to be mixable with polyisocyanates in a reliable and easy manner.

The reaction which is used to prepare polyaspartates is the addition of primary amines to the activated C—C double bond in vinyl carbonyl compounds, which has been described in the literature (see Chem. Ber. 1946, 38,83; Houben Weyl, Meth. d. Org. Chemie, Vol. 11/1, 272 (1957); Usp. Chimil 1969, 38, 1933). It has been found, however, that this reaction does not proceed to completion during the course of the actual synthesis process (e.g., 24 hours with stirring at 60° C.). The actual extent of the reaction is dependent upon the type of primary polyamine. Thus, the degree of conversion (measured by the concentration of free, unconverted maleate and fumarate, into which maleate rearranges in the presence of basic catalysts) after 1 day with 1,6-hexanediamine is about 90 to 93%. The degree of conversion after 1 day with a cycloaliphatic polyamine having sterically hindered primary amino groups, i.e., 4,4'-diamino-3,3'-dimethyldicyclohexylmethane is only 77% Complete or essentially complete conversion is achieved only after several days or, in the case of 4,4'-diamino-3,3'-dimethyldicyclohexyl-methane, only after several months.

In a typical commecial production, the reaction is run for sixteen hours when the conversion is somewhere between 75 and 95% complete depending on the amine used. The "unfinished" material is drummed and held in storage until the reaction is complete. This typically takes anywhere from two weeks to six months. U.S. Pat. No. 5,821,326 describes the use of certain five-membered aromatic ring compounds as catalyst to accelerate the preparation of the aspartates.

The conventional aspartates are capable of a further transformation (after curing with an isocyanate) to form a hydantoin ring structure. This hydantoin formation might lead to a shrinking of the coating and undesired alcohol formation. It would also be desirable to prepare an aspartate that would be less prone to hydantoin formation.

DESCRIPTION OF THE INVENTION

The present invention is directed to novel aspartates of the formula:

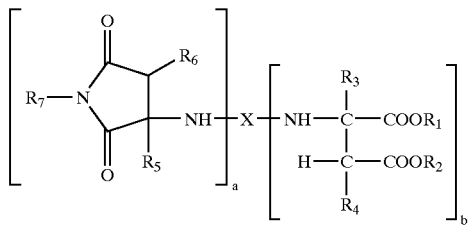

where

X represents an m-valent organic residue obtained by removing the primary amino group or groups from a di- or polyamine containing primary amino groups and having a number average molecular weight of 60 to 6000, and which may contain further functional groups that either are reactive with isocyanate groups or are inert to isocyanate groups at temperatures of up to 100° C., $R_3$ and $R_4$ may be identical or different and represent hydrogen or organic groups which are inert towards isocyanate groups at a temperature of 100° C. or less (both are preferably hydrogen), $R_1$ and $R_2$ may be identical or different and represent organic groups which are inert towards isocyanate groups at a temperature of 100° C. or less (preferably a $C_1$ to $C_8$ alkyl and most preferably methyl or ethyl), $R_5$ and $R_6$ may be the same or different and represent moieties selected from the group consisting of i) hydrogen, ii) straight or branched $C_1$ to $C_8$ alkyl groups, which may be substituted with up to three aryl groups containing from 6 to 10 carbon atoms, iii) $C_6$ to $C_{10}$ aryl groups, which may be substituted with up to three alkyl groups having from 1 to 3 carbon atoms, and iv) together form a six-membered cycloalkyl group, with said cycloalkyl group being substituted with from 0 to 3 alkyl groups having from 1 to 3 carbon atoms, $R_7$ represents a moiety selected from the group consisting of i) hydrogen, ii) straight or branched $C_1$ to $C_8$ alkyl groups, which may be substituted with up to three aryl groups containing from 6 to 10 carbon atoms, and iii) $C_6$ to $C_{10}$ aryl groups, which may be substituted with up to three alkyl groups having from 1 to 3 carbon atoms, a and b represent integers of from 1 to 5, provided that the sum of a and b is from 2 to 6.

The products of the present invention, when combined with a polyisocyanate, have longer potlifes and provide for harder coatings than aspartates of the prior art. In addition, the products have less of a tendency to form hydantoin rings.

The present invention also relates to a process for preparing aspartates of the above formula comprising A) reacting at a temperature of 0 to 100° C., in solution or in the absence of a solvent and at an equivalent ratio of primary amino groups in component a) to C=C double bonds in component b) of from about 1.1:1 to about 3.0:1
a) di- or polyamines corresponding to formula (II)

$$X[-NH_2]_m \quad (II)$$

with
b) compounds corresponding to formula (III)

$$R_1OOC-C(R_3)=C(R_4)-COOR_2 \quad (III)$$

wherein
X, $R_1$, $R_2$, $R_3$ and $R_4$ are as defined above and m represents an integer of from 2 to 6, and
B) reacting the resultant product with a maleimide.

The present invention also relates to a two-component coating composition which contains, as binder,
a) a polyisocyanate component and
b) an isocyanate-reactive component containing
b1) a compound corresponding to formula (I) and
b2) optionally other isocyanate-reactive compounds, wherein the equivalent ratio of isocyanate groups to isocyanate-reactive groups is from about 0.8:1 to about 2:1, and optionally, additives known in surface coatings technology.

Finally, the present invention also relates to prepolymers containing urea, urethane, allophanate and/or biuret structures, which are based on the reaction product of polyisocyanates with the aspartates of the invention, optionally in admixture with one or more isocyanate-reactive components.

The polyamines useful herein include i) high molecular weight amines having molecular weights of 400 to about 10,000, preferably 800 to about 6,000, and ii) low molecular weight amines having molecular weights below 400. The molecular weights are number average molecular weights ($M_n$) and are determined by end group analysis (NH number). Examples of these polyamines are those wherein the amino groups are attached to aliphatic, cycloaliphatic, araliphatic and/or aromatic carbon atoms.

Suitable low molecular polyamine starting compounds include ethylene diamine, 1,2- and 1,3-propane diamine, 2-methyl-1,2-propane diamine, 2,2-dimethyl-1,3-propane diamine, 1,3- and 1,4-butane diamine, 1,3- and 1,5-pentane diamine, 2-methyl-1,5-pentane diamine, 1,6hexane diamine, 2,5-dimethyl-2,5hexane diamine, 2,2,4-and/or 2,4,4-trimethyl-1,6-hexane diamine, 1,7-heptane diamine, 1,8-octane diamine, 1,9-nonane diamine, 1,10-decane diamine, 1,11-undecane diamine, 1,12-dodecane diamine, 1-amino-3-aminomethyl-3,5,5-trimethyl cyclohexane, 2,4- and/or 2,6-hexahydrotoluylene diamine, 2,4'- and/or 4,4'-diamino-dicyclohexylmethane, 3,3'-dialkyl-4,4'-diamino-dicyclohexyl methanes (such as 3,3'-dimethyl-4,4'-diarmino-dicyclohexyl methane and 3,3'-diethyl-4,4'-diamino-dicyclohexyl methane), 1,3- and/or 1,4-cyclohexane diamine, 1,3-bis(methylamino)-cyclohexane, 1,8-p-menthane diamine, hydrazine, hydrazides of semicarbazido carboxylic acids, bis-hydrazides, bis-semicarbazides, phenylene diamine, 2,4- and 2,6-toluylene diamine, 2,3-and 3,4-toluylene diamine, 2,4'- and/or 4,4'-diaminodiphenyl methane, higher functional polyphenylene polymethylene polyamines obtained by the aniline/formaldehyde condensation reaction, N,N,N-tris-(2-amino-ethyl)-amine, guanidine, melamine, N-(2-aminoethyl)-1,3-propane diamine, 3,3'-diamino-benzidine, polyoxypropylene amines, polyoxy-ethylene amines, mixed propylene oxide/ethylene oxide diamines (such as 3,3'-[1,2-ethanediylbis(oxy)]bis (1-propaneamine)), 2,4-bis-(4'-aminobenzyl)-aniline and mixtures thereof.

Preferred polyamines are 1-amino-3aminomethyl-3,5,5-trimethyl-cyclohexane (isophorone diamine or IPDA), bis-(4-aminocyclohexyl)-methane, bis-(4-amino-3-methylcyclohexyl)-methane, 1,6-diamino-hexane, 2-methyl pentamethylene diamine, ethylene diamine and 3,3'-[1,2-ethanediylbis(oxy)]bis (1-propaneamine).

Suitable high molecular weight polyamines correspond to the polyhydroxyl compounds used to prepare the NCO prepolymers with the exception that the terminal hydroxy groups are converted to amino groups, either by amination or by reacting the hydroxy groups with a diisocyanate and subsequently hydrolyzing the terminal isocyanate group to an amino group. Preferred high molecular weight polyamines are amine-terminated polyethers such as the Jeffamine resins available from Huntsman.

Suitable optionally substituted maleic or fumaric acid esters for use in the preparation of the aspartates are those corresponding to the formula $$R_1OOC-C(R_3)=C(R_4)-COOR_2$$

wherein $R_3$, $R_4$, $R_5$ and $R_6$ are as previously defined. Examples include the dimethyl, diethyl, di-n-butyl and mixed alkyl esters of maleic acid and fumaric acid and the corresponding maleic or fumaric acid esters substituted by methyl in the 2- and/or 3-position. Suitable maleates or fumarates for preparing the aspartates of the present invention include dimethyl, diethyl, di-n-propyl, di-isopropyl, di-n-butyl and di-2-ethylhexyl maleates, methylethylmaleate or the corresponding fumarates.

The aspartates of the present invention are prepared by first reacting component Aa) with component Ab) at temperatures of 0 and 100° C., preferably 20 to 80° C. and more preferably 20 to 60° C. wherein (i) the equivalent ratio of primary amino groups in component a) to C=C double bond equivalents in component b) is from about 1.1:1 to about 3.0:1, preferably from about 1.1:1 to about 2.0:1. The reaction time may vary from about 1 to about 4 hours, depending upon the type of polyamine and the desired maximum residual concentration of reactants in the reaction mixture. The resultant product is then reacted with a maleimide.

Useful maleimides are those of the structure:

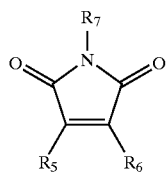

where $R_5$, $R_6$, and $R_7$ are as defined above. Specifically useful maleimides include N-methyl maleimide, N-ethyl maleimide, N-propyl maleimide, N-isopropyl maleimide, N-isobutyl maleimide, N-butyl maleimide, N-amyl maleimide, N-ethylamyl maleimide, N-methylisoamyl maleimide, N-methylhexyl maleimide, N-phenyl maleimide, N-ethyl-2-methylmaleimide, N-2,3-trimethyl maleimide, 3-methyl-N-phenyl maleimide, N-phenyl-3,4,5,6-tetrahydrophthalimide and 3-phenyl-N-phenyl maleimide.

This second reaction is typically conducted at a temperature of from about 50 to about 100° C., for times ranging from about 1 to about 4 hours. The ratio of reactants is chosen so that at least one mole of maleimide is present for each unreacted amine group. The excess maleimide can then be removed to give a 100% resinous product, or it can remain and can serve as a solvent.

The process to prepare the aspartates of the present invention may either be performed in solution or in the absence of a solvent. Solvent may also be added after the synthesis process, for example, to lower the viscosity. Suitable solvents include any organic solvents, preferably those known from surface coating technology. Examples include acetone, methyl ethyl ketone, methyl isobutyl ketone, n-butyl acetate, methoxy-propyl acetate, toluene, xylene, and higher aromatic solvents (such as the Solvesso solvents from Exxon).

The aspartates prepared according to the invention may be directly used as reactive components for polyisocyanates after concluding the synthesis process.

One use of the aspartates of the present invention is to prepare coatings from two-component coating compositions containing, as binder, a) a polyisocyanate component and
b) an isocyanate-reactive component containing
   b1) the aspartates of the invention and
   b2) optionally other known isocyanate-reactive components.

Suitable polyisocyanate components a) are known and include the polyisocyanates known from polyurethane chemistry, e.g., low molecular weight polyisocyanates and lacquer polyisocyanates prepared from these low molecular weight polyisocyanates. Preferred are the lacquer polyisocyanates, which are known from surface coating technology. These lacquer polyisocyanates contain biuret groups, isocyanurate groups, allophanate groups, uretdione groups, carbodiimide groups and/or urethane groups and are preferably prepared from (cyclo)aliphatic polyisocyanates.

Suitable low molecular weight polyisocyanates for use in accordance with the present invention or for preparing the lacquer polyisocyanates are those having a molecular weight of 140 to 300, such as 1,4-tetramethylene diisocyanate, 1,6-hexamethylene diisocyanate (HDI), 2,2,4- and/or 2,4,4-trimethyl-hexamethylene diisocyanate, dodecamethylene diisocyanate, 2-methyl-1,5-diisocyanatopentane, 1,4-diisocyanatocyclohexane, 1-isocyanato-3,3,5-trimethyl-5-isocyanato-methylcyclohexane (IPDI), 2,4- and/or 4,4' diisocyanato-dicyclohexyl-methane, 1 -isocyanato-1 -methyl-3(4)-isocyanatomethyl-cyclohexane (IMCI), 2,4- and/or 2,6-hexahydrotoluylene diisocyanate ($H_6TDI$), 2,4- and/or 4,4'-diisocyanatodiphenylmethane or mixtures of these isomers with their higher homologs (which may be obtained in known manner by the phosgenation of anilinel-formaldehyde condensates), 2,4and/or 2,6-diisocyanatotoluene, and mixtures thereof. The use of low molecular weight polyisocyanates themselves is not preferred. Also, lacquer polyisocyanates prepared from aromatic polyisocyanates, such as 2,4-and/or 2,6diisocyanatotoluene, are also less preferred. The lacquer polyisocyanates containing urethane groups are preferably based on low molecular weight polyhydroxyl compounds having molecular weights of 62 to 300, such as ethylene glycol, propylene glycol and/or trimethylol-propane.

Preferred lacquer polyisocyanates for use as component a) are those based on 1,6-hexamethylene diisocyanate and having an NCO content of 16 to 24 wt. % and a maximum viscosity at 23° C. of 10,000, preferably 3,000 mPa.s.

Component b1) is selected from the aspartates of the present invention. Preferably, X represents a divalent hydrocarbon group obtained by removing the amino groups from 1 -amino-3-aminomethyl-3,5,5-trimethyl-cyclohexane (isophorone diamine or IPDA), bis-(4-aminocyclo-hexyl)-methane, bis-(4-amino-3-methylcyclohexyl)-methane, 1,6-diamino hexane, 2-methyl pentamethylene diamine, ethylene diamine and 3,3'-[1,2-ethanedlylbis(oxy)]bis (1-propaneamine).

Particularly preferred starting components b1) include those aspartates in which $R_1$ and $R_2$ represent $C_1$ to $C_8$ alkyl groups such as methyl, ethyl, n-propyl, isopropyl, n-butyl or 2-ethylhexyl.

Optional starting components b2) are known compounds containing at least two isocyanate-reactive groups, including groups which react with isocyanate groups under the effect of either moisture or/and heat. Examples include hydroxy-functional polyacrylates and polyesterpolyols Mixtures of these compounds may also be used.

In the binders used according to the invention, the amounts of components a), b1) and (optionally) b2) are selected such that the equivalent ratio isocyanate groups to isocyanate-reactive groups is from about 0.8:1 to about 2.0:1, and preferably from about 0.8:1 to about 1.2:1.

The binders according to the invention are prepared by mixing the individual components either in the absence of a solvent or in the presence of the solvents which are conventionally used in polyurethane surface coating technology. Suitable solvents include ethyl acetate, butyl acetate, methoxypropyl acetate, methyl isobutyl ketone, methyl ethyl ketone, xylene, N-methylpyrrolidone, petroleum spirit, chlorobenzene, Solvesso solvent or mixtures thereof.

Preferably, the ratio by weight of binder components a) and b) to solvent in the coating compositions according to the invention is from about 40:60 to about 100:0, more preferably from about 60:40 to about 100:0.

The coating compositions may also contain the known additives from surface coating technology. These include pigments, fillers, flow control agents, catalysts and anti-settling agents.

The properties of the coatings obtained from the coating compositions according to the invention may be adjusted by appropriate selection of the type and ratios of starting components a), b1) and b2).

The coating compositions may be applied to any substrate in a single layer or in several layers by known methods, e.g., by spraying, painting, immersing, flooding or by using rollers or spreaders. The coating compositions according to the invention are suitable for preparing coatings on substrates, such as metals, plastics, wood or glass. The coating compositions are especially suitable for coating steel sheeting, which is used for the production of vehicle bodies, machines, cladding panels, barrels and containers. The substrates may be provided with suitable primer coats prior to applying the coating compositions according to the Invention. Drying of the coatings may take place at a temperature of about 0 to 1 60° C.

The process for producing coatings using the aspartates of the present invention may also be used for the production of prepolymers containing urea, urethane, allophanate and/or biuret structures.

The aspartates of the present invention may be directly used after completion of the synthesis process because, in contrast to prior art aspartates, an approximately complete degree of conversion is achieved. As a result of the low concentration of maleates, fumarates and primary amino groups, these products are toxicologically and physiologically harmless. They also exhibit a reasonable, as opposed to a vigorous, reactivity towards isocyanates. Due to their low viscosity, they are a more than suitable alternative, as reactive diluents, to the environmentally polluting organic solvents previously used and may therefore be used in high quality, low-solvent or even solvent-free, high solids, two-component coating compositions.

All parts and percentages in the examples which follow are by weight, unless otherwise indicated.

EXAMPLE 1

A round bottom flask was fitted with stirrer, heating mantle, nitrogen inlet, thermocouple and addition funnel. 58 parts (1.0 eq.) of 2-metyl-1,5-pentandiamine was added to the flask at room temperature. 137.7 parts (0.8 eq.) of diethyl maleate was-added through the addition funnel over a period of sixty minutes. The temperature of the flask rose to 35° C. The reaction was heated to 60° C. and held for seven hours at which time an iodometric titraton showed that the reaction was complete. The reaction mixture was cooled to room temperature. 25.02 parts (0.2 eq.) of N-ethylmaleimide was added. The temperature was held at 25° C. for eight hours until the reaction was complete. The clear, nearly colorless final product had a viscosity of 260 cps and an amine number of 251 (theoretical amine number: 253).

EXAMPLE 2

A round bottom flask was fitted with stirrer, heating mantle, nitrogen inlet, thermocouple and addition funnel. 105 parts (1.0 eq.) of bis-(para-aminocyclohexyl)methane was added to the flask at room temperature. 129 parts (0.75 eq.) of diethyl maleate was added through the addition funnel over a period of sixty minutes. The temperature of the flask rose to 33° C. The reaction was heated to 60° C. and held for ten hours at which time an iodometric titration showed that the reaction was complete. The reaction mixture was cooled to room temperature. 31.28 parts (0.25 eq.) of N-ethylmaleimide was added. The temperature was held at 25° C. for eight hours, after which time the reaction was complete. The clear, nearly colorless final product had a viscosity of 6300 cps and an amine number of 209 (theoretical amine number: 211).

EXAMPLE 3

A round bottom flask was fitted with stirrer, heating mantle, nitrogen inlet, thermocouple and addition funnel. 85 parts (1.0 eq.) of 5-amino-1,3,3-trimethylcyclohexanemethylamine ("isophorone diamine") was added to the flask at room temperature. 137.7 parts (0.80 eq.) of diethyl maleate was added through the addition funnel over a period of sixty minutes. The temperature of the flask rose to 35° C. The reaction was heated to 60° C. and held for ten hours at which time an iodometric titration showed that the reaction was complete. The reaction mixture was cooled to room temperature. 25.1 parts (0.20 eq.) of N-ethylmaleimide was added. The temperature was held at 25° C. for eight hours, after which time the reaction was complete. The clear, nearly colorless final product had a viscosity of: 2070 cps and an amine number of 223 (theoretical amine number: 227).

The samples from the Examples were hand mixed with Desmodur N-3300 (a trimerized hexane diisocyanate having an NCO content of 21.8% and an equivalent weight of 192), at a NCO to NH equivalent ratio of 1. Viscosity was measured on a Brookfield Viscometer. Sample drytime was measured by doing a drawdown of the mixed sample on glass. Samples were drawn down at 10 mils wet. At 2 minute intervals, a cotton ball was pressed on the drawdown to test for film cure. The sample film was completely cured when the cotton ball did not leave an imprint. Shore D Hardness was measured by pouring the mixed sample into an aluminum cup and testing for hardness 3 days later with a Shore Durometer Type D-2, ASTM D2240. Results were as reported in the following table:

|  | Drytime, minutes | Potlife, mins. | Shore D | Appearance of film |
|---|---|---|---|---|
| Example 1 | <2 | <2 | 79 | Clear |
| Example 2 | 10 | 8 | 75 | Clear |
| Example 3 | 25 | 20 | 75 | Clear |

(Shore D hardness–3 days after mix)

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. An aspartate of the formula:

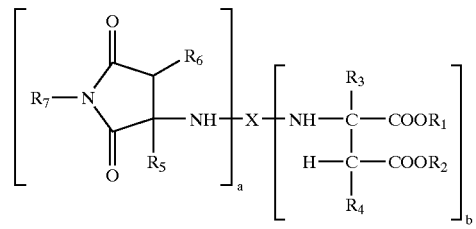

where
  x represents an m-valent organic residue obtained by removing the primary amino group or groups from a di- or polyamine containing primary amino groups and having a number average molecular weight of 60 to 6000, and which may contain further functional groups that either are reactive with isocyanate groups or are inert to isocyanate groups at temperatures of up to 100° C.,
  $R_3$ and $R_4$ may be identical or different and represent hydrogen or organic groups which are inert towards isocyanate groups at a temperature of 100° C. or less,
  $R_1$ and $R_2$ may be identical or different and represent organic groups which are inert towards isocyanate groups at a temperature of 100° C. or less,
  $R_5$ and $R_6$ may be the same or different and represent moieties selected from the group consisting of i) hydrogen, ii) straight or branched $C_1$ to $C_8$ alkyl groups, which may be substituted with up to three aryl groups containing from 6 to 10 carbon atoms, iii) $C_6$ to $C_{10}$ aryl groups, which may be substituted with up to three alkyl groups having from 1 to 3 carbon atoms, and iv) together form a six-membered cycloalkyl group, with said cycloalkyl group being substituted with from 0 to 3 alkyl groups having from 1 to 3 carbon atoms, R₇ represents a moiety selected from the group consisting of i) hydrogen, ii) straight or branched $C_1$ to $C_8$ alkyl groups, which may be substituted with up to three aryl groups containing from 6 to 10 carbon atoms, and iii) $C_6$ to $C_{10}$ aryl groups, which may be substituted with up to three alkyl groups having from 1 to 3 carbon atoms, a and b represent integers of from 1 to 5, provided that the sum of a and b is from 2 to 6.

2. The aspartate of claim 1, wherein X represents a divalent hydrocarbon group obtained by removing the amino groups from 1-amino-3-aminomethyl-3,5,5-trimethyl-cyclohexane (isophorone diamine or IPDA), bis-(4-aminocyclohexyl)-methane, bis-(4-amino-3-methylcyclohexyl)-methane, 1,6diamino-hexane, 2-methyl pentamethylene diamine, ethylene diamine or 3,3'-[1,2-ethanediylbis(oxy)]bis(1-propaneamine).

3. The aspartate of claim 1, wherein $R_3$ and $R_4$ are hydrogen.

4. The aspartate of claim 1, wherein $R_1$ and $R_2$ are each alkyl groups having from 1 to 8 carbon atoms.

5. A process for preparing an aspartate of the formula:

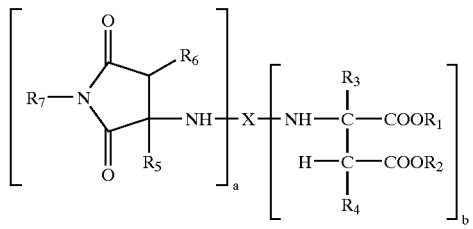

where

X represents an m-valent organic residue obtained by removing the primary amino group or groups from a di- or polyamine containing primary amino groups and having a number average molecular weight of 60 to 6000, and which may contain further functional groups that either are reactive with isocyanate groups or are inert to isocyanate groups at temperatures of up to 100° C., $R_3$ and $R_4$ may be identical or different and represent hydrogen or organic groups which are inert towards isocyanate groups at a temperature of 100° C. or less, $R_1$ and $R_2$ may be identical or different and represent organic groups which are inert towards isocyanate groups at a temperature of 100° C. or less, $R_5$ and $R_6$ may be the same or different and represent moieties selected from the group consisting of i) hydrogen, ii) straight or branched $C_1$ to $C_8$ alkyl groups, which may be substituted with up to three aryl groups containing from 6 to 10 carbon atoms, iii) $C_6$ to $C_{10}$ aryl groups, which may be substituted with up to three alkyl groups having from 1 to 3 carbon atoms, and iv) together form a six-membered cycloalkyl group, with said cycloalkyl group being substituted with from 0 to 3 alkyl groups having from 1 to 3 carbon atoms, R₇ represents a moiety selected from the group consisting of i) hydrogen, ii) straight or branched $C_1$ to $C_8$ alkyl groups, which may be substituted with up to three aryl groups containing from 6 to 10 carbon atoms, and iii) $C_6$ to $C_{10}$ aryl groups, which may be substituted with up to three alkyl groups having from 1 to 3 carbon atoms, a and b represent integers of from 1 to 5, provided that the sum of a and b is from 2 to 6, comprising A) reacting at a temperature of 0 to 100° C., in solution or in the absence of a solvent and at an equivalent ratio of primary amino groups in component a) to C=C double bonds in component b) of from about 1.1:1 to about 3.0:1 a) di- or polyamines corresponding to formula (II)

with b) compounds corresponding to formula (III)

wherein

X, $R_1$, $R_2$, $R_3$ and $R_4$ are as defined above and m represents an integer of from 2 to 6, and B) reacting the resultant product with a maleimide.

6. The process of claim 5, wherein X represents a divalent hydrocarbon group obtained by removing the amino groups from 1-amino-3-aminomethyl-3,5,5-trimethylcyclohexane (isophorone diamine or IPDA), bis-(4-aminocyclohexyl)-methane, bis-(4-amino-3-methylcyclohexyl)-methane, 1,6-diamino-hexane, 2-methyl pentamethylene diamine, ethylene diamine or 3,3'-[1,2-ethanediylbis(oxy)]bis(1-propaneamine).

7. The process of claim 5, wherein $R_3$ and $R_4$ are hydrogen.

8. The process of claim 5, wherein $R_1$ and $R_2$ are each alkyl groups having from 1 to 8 carbon atoms.

9. The process of claim 5, wherein said maleimide is of the formula:

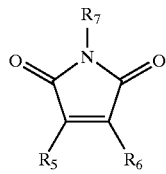

where $R_5$, $R_6$ and $R_7$ are as defined above.

10. A two-component coating composition which comprises, as binder, a) a polyisocyanate component and b) an isocyanate-reactive component containing b1) the aspartate of claim 1, b2) optionally other isocyanate-reactive compounds, wherein the equivalent ratio of isocyanate groups to isocyanate-reactive groups is from about 0.8:1 to about 2.0:1.

11. A prepolymer containing urea, urethane, allophanate and/or biuret structures comprising the reaction product of a polyisocyanate with the aspartate of claim 1.

* * * * *